United States Patent [19]

Marano

[11] Patent Number: 5,722,951
[45] Date of Patent: Mar. 3, 1998

[54] HYPODERMIC NON-REUSABLE SYRINGES WITHOUT VOLUNTARY INTERVENTION OF THE USER

[76] Inventor: Carlos José Marano, Máximo paz 497, Buenos Aires, Argentina, 1824

[21] Appl. No.: 501,666

[22] Filed: Jul. 12, 1995

[30] Foreign Application Priority Data

Jul. 14, 1994 [AR] Argentina ................. 328.803
Jul. 11, 1995 [AR] Argentina ................. 332.722

[51] Int. Cl.⁶ ............................................ A61M 5/00
[52] U.S. Cl. .......................... 604/110; 604/218; 604/228
[58] Field of Search ........................ 604/187, 110, 604/218, 220, 228

[56] References Cited

U.S. PATENT DOCUMENTS

| | | | |
|---|---|---|---|
| 4,883,466 | 11/1989 | Glazier | 604/228 X |
| 5,181,912 | 1/1993 | Hammett | 604/110 |
| 5,195,975 | 3/1993 | Castagna | 604/218 X |
| 5,290,235 | 3/1994 | Polyblank et al. | 604/110 |

*Primary Examiner*—John D. Yasko
*Attorney, Agent, or Firm*—Darby & Darby

[57] ABSTRACT

An autodiscardable hypodermic syringe having a preset piston stroke limitation includes an elongated cylinder having an opened end an opposite substantially closed end. A conduit of an external tubular mouth piece for coupling with the needle is connected to the substantially closed end of the cylinder. A piston is slidably received within the cylinder. A rod for sliding the piston is selectively connected to the piston. An end of the rod remote from the piston projects beyond the open end of the cylinder. The piston is selectively connected to the rod through a coupling and uncoupling mechanism. The coupling and uncoupling mechanism includes a narrow body that projects from the internal end of the rod and has a passage coincident with a central axis of the rod. The passage extends from side to side of the narrow body and defines a descending section that in its middle part has a deviation disposed outward of the descending section and of the narrow body. The piston is provided with a cavity to house the narrow body. The piston is also provided with a hook disposed within the passage that is capable of being displaced from the descending section and outward through the deviation during expulsion movements respectfully. Additionally, the syringe includes a retention device for retaining the rod in the cylinder that is provided within the cylinder of the syringe in an area that does not impede with the normal operation of the piston and rod.

10 Claims, 6 Drawing Sheets

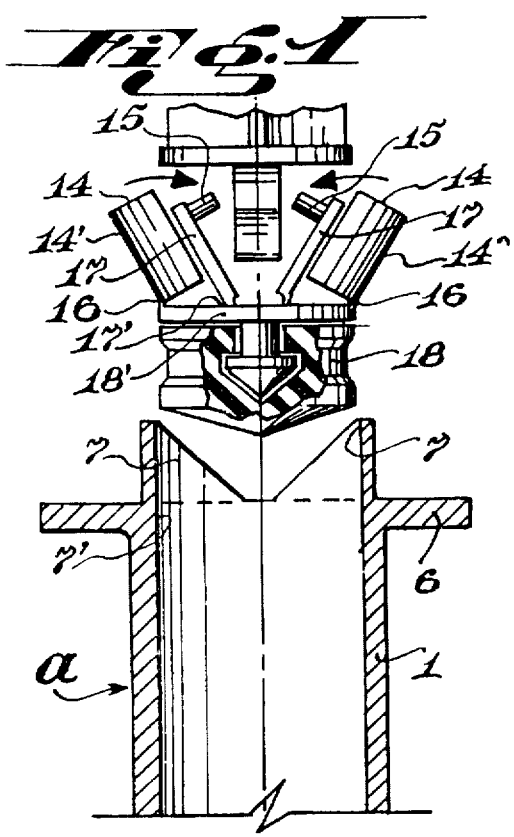
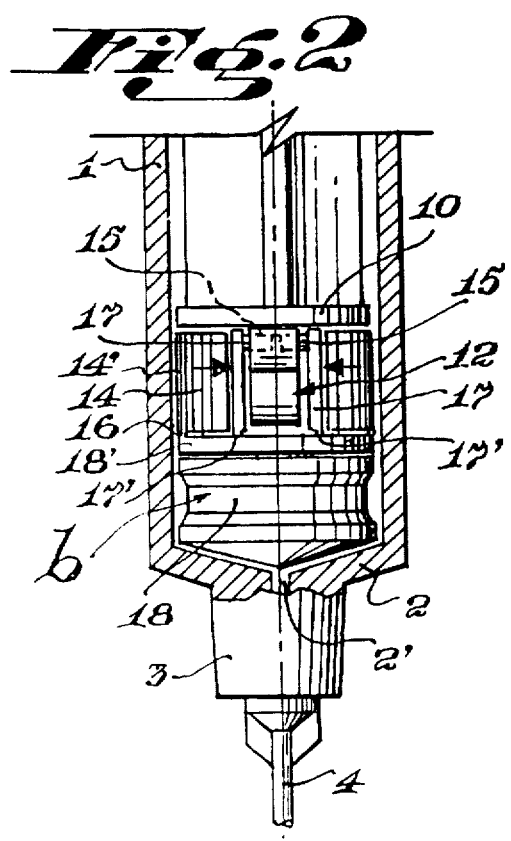
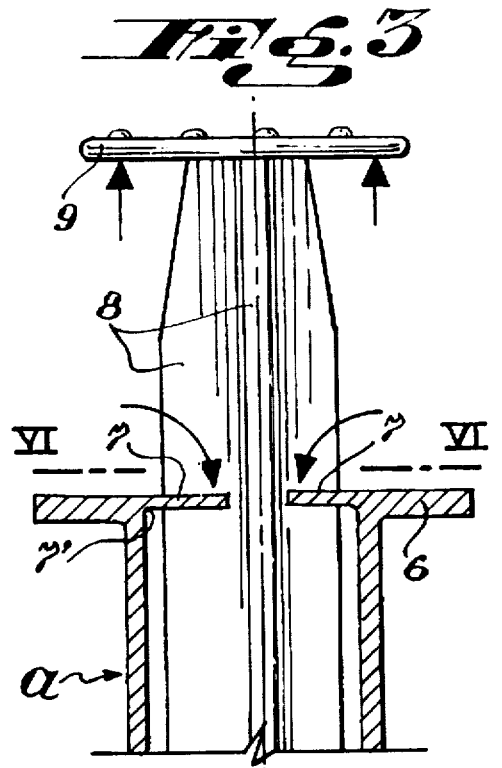
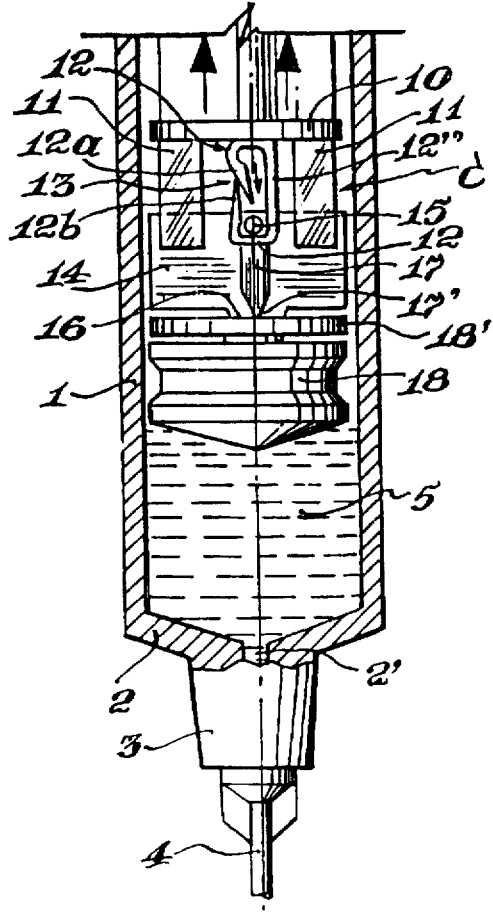

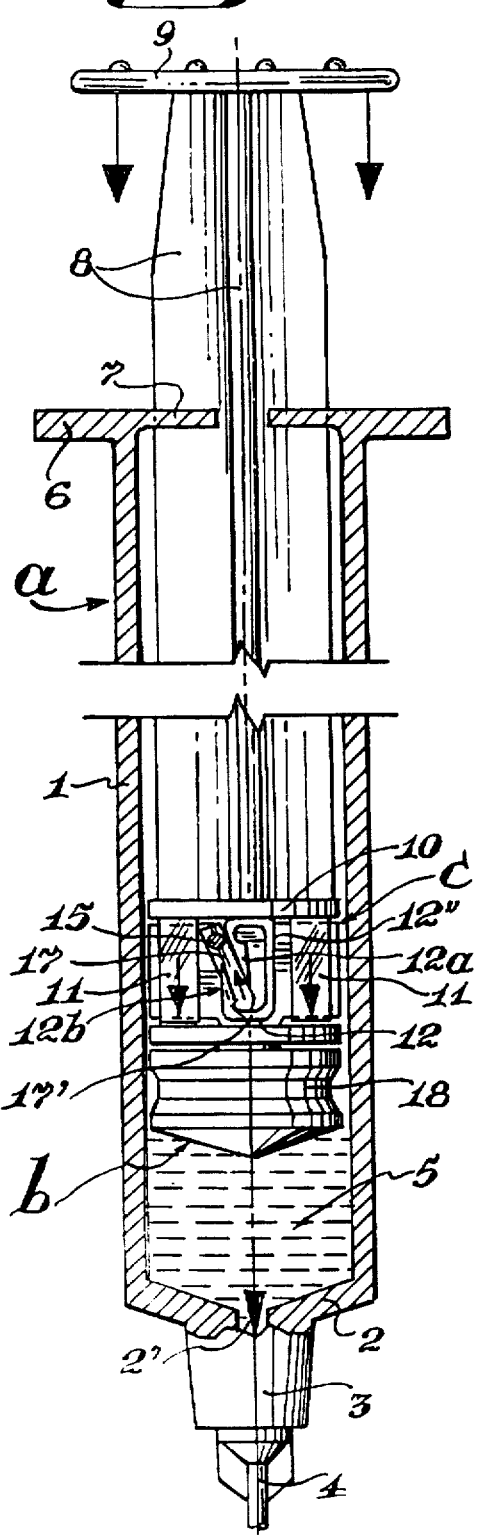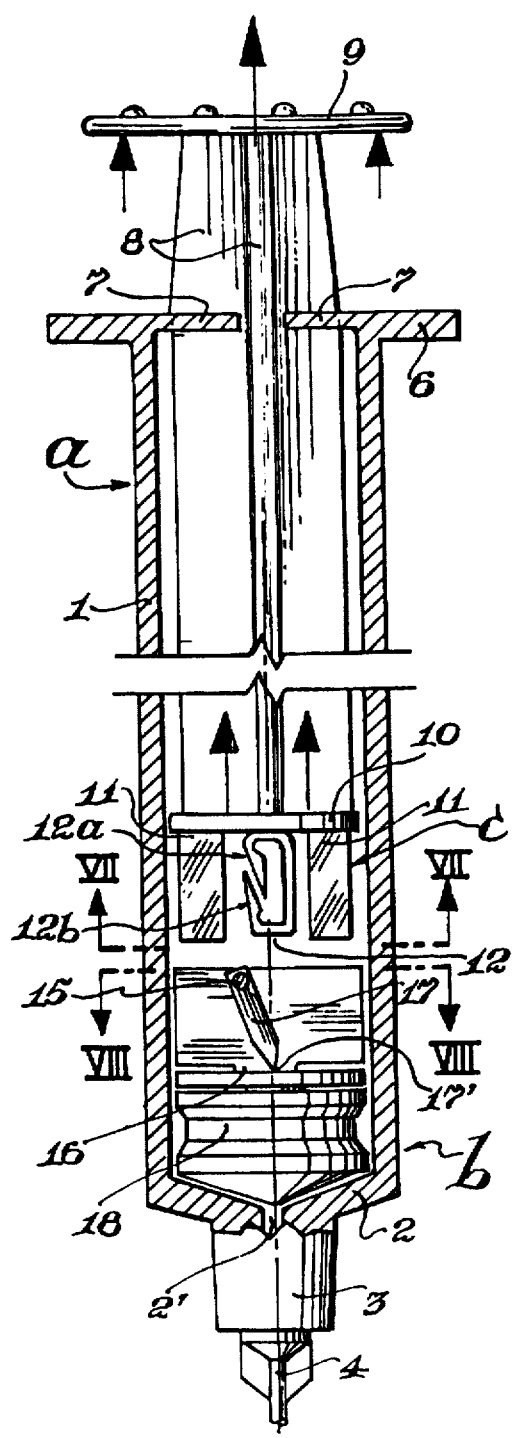

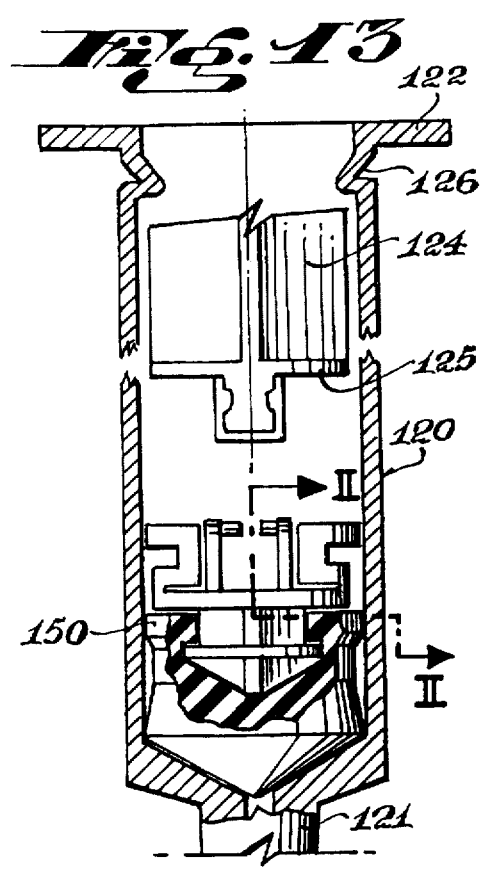
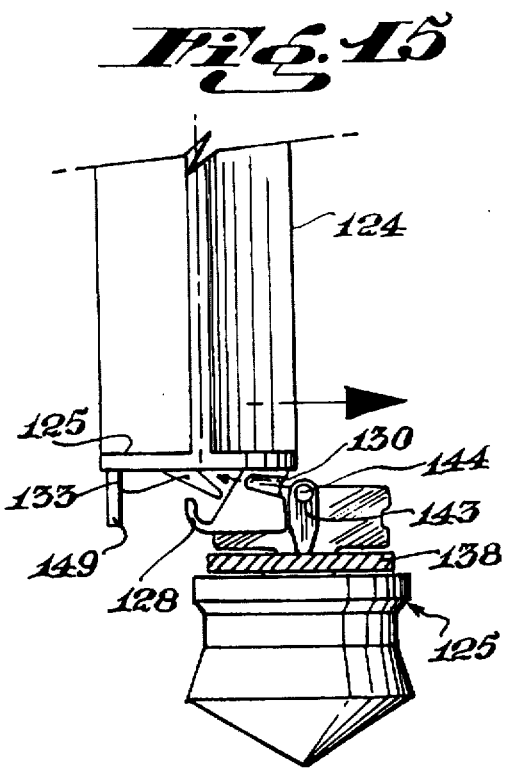
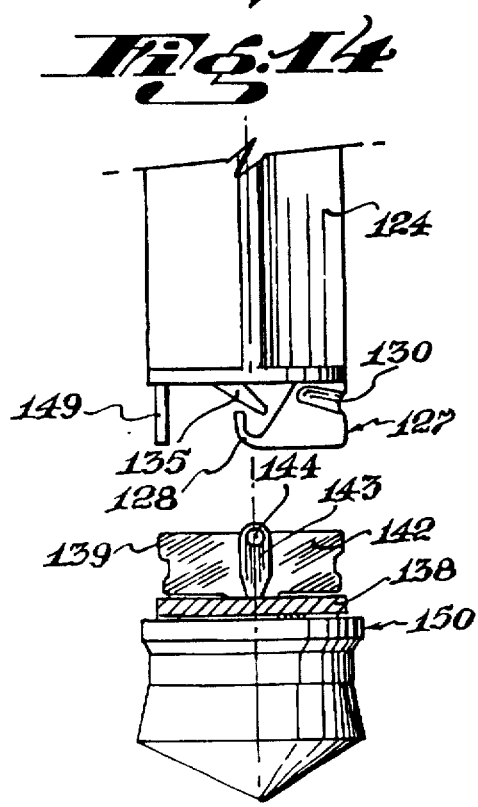
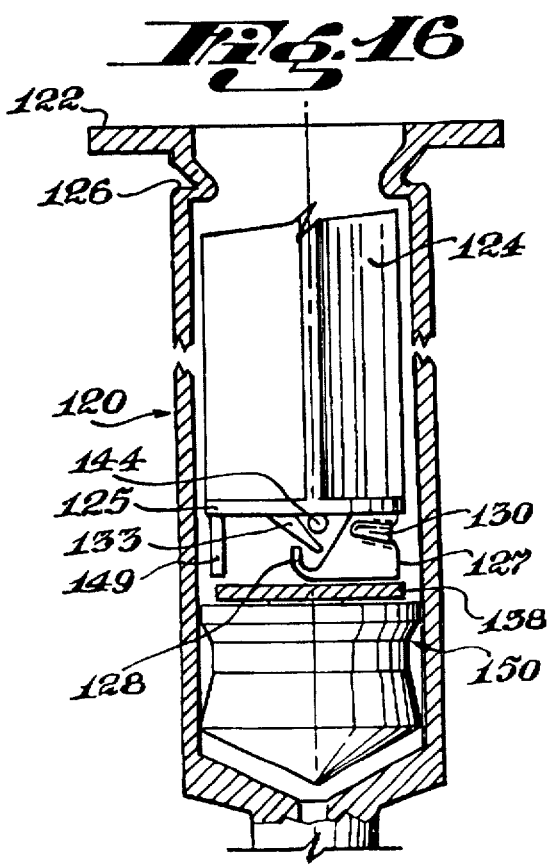

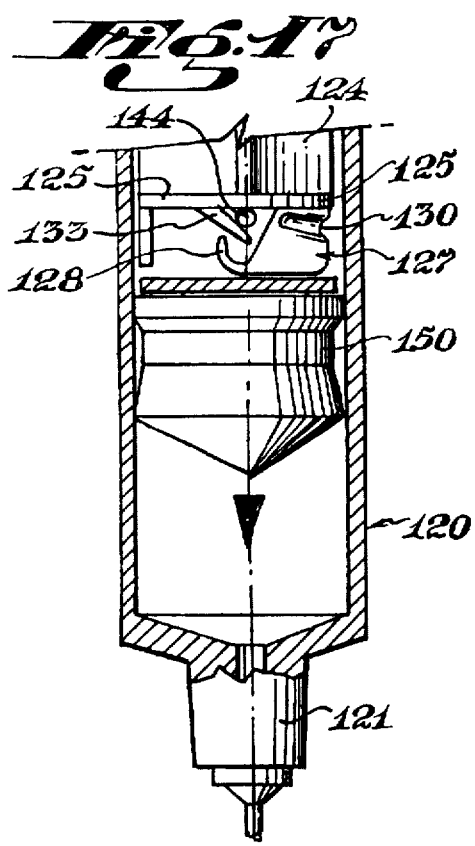
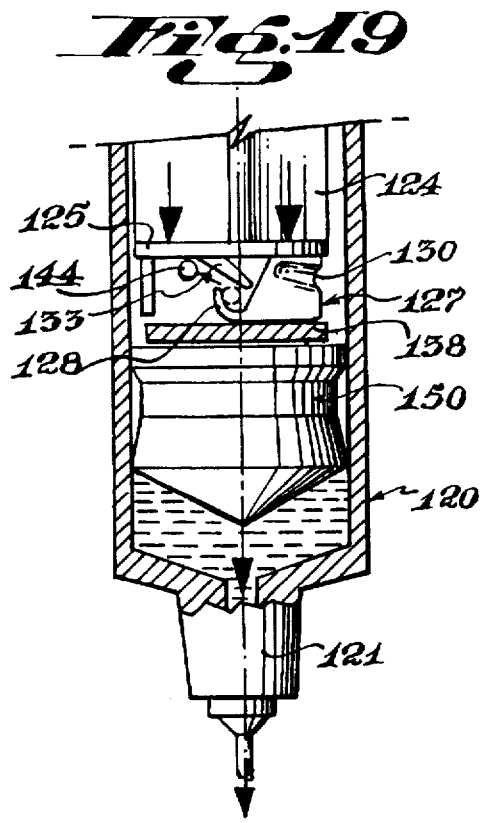
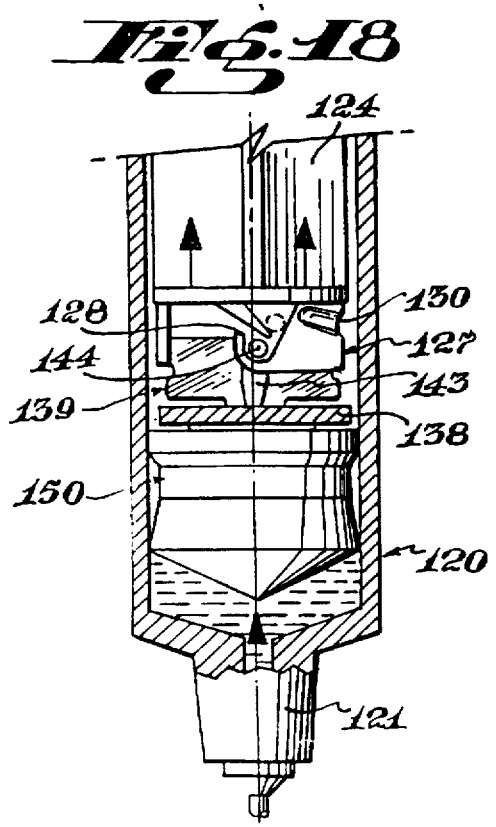
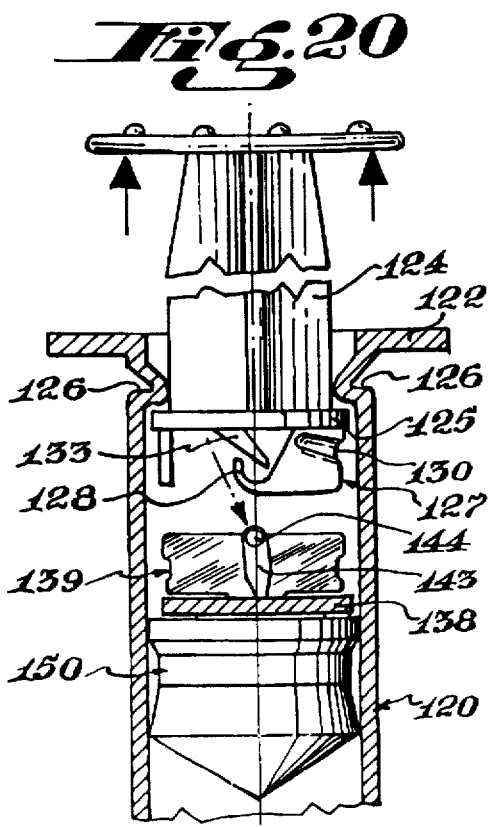

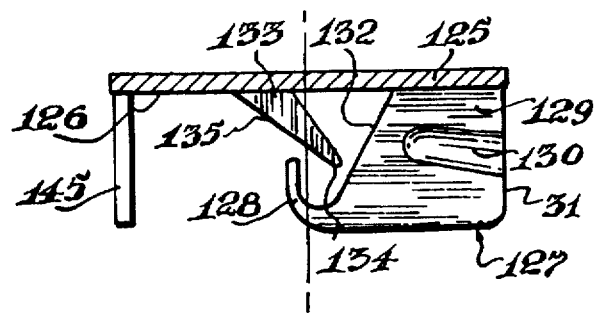
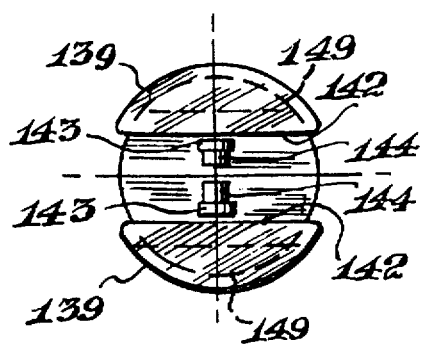
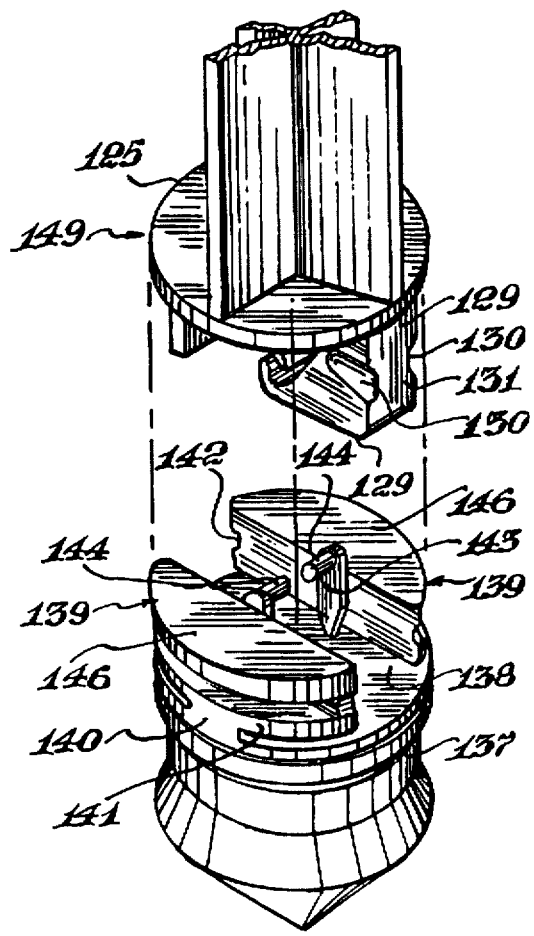
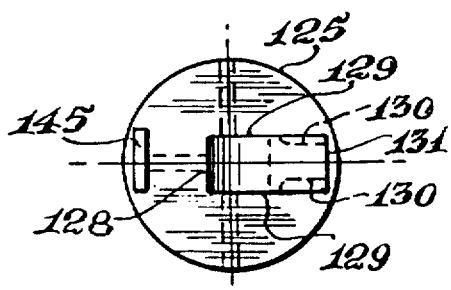

5,722,951

HYPODERMIC NON-REUSABLE SYRINGES WITHOUT VOLUNTARY INTERVENTION OF THE USER

BACKGROUND OF THE INVENTION

This invention relates to improvements in hypodermic non-reusable syringes, by the normal operation of the syringe without voluntary intervention of the user with predetermined limitation of strokes, as well as the method of quick preparation of the syringes for its industrial production. The object of this invention is to provide a new syringe that, due to the way it has been developed, cannot be reused. Therefore, the syringe is non-reusable, despite the user's desire.

It is not necessary to explain many details to understand the importance that a syringe fitting these characteristics implies, as it assures the fact that it will be used by a single person without the possibility of being reused; for once the suction and the ejection of the corresponding medicine have been made, the same becomes useless. In this way, the transmission of diseases as serious as AIDS, hepatitis and blood contagion ones between an infected patient that uses it first, and a healthy one that reuses it afterwards, is avoided.

Precisely, owing to the information provided by these diseases, it is known that one of the ways that imply the greatest risk of contagion is by reusing hypodermic syringes. Devices that intend to allow the disposal of the syringe such as boxes and containers which allow the insertion of syringes and needles, but obstruct their outlet, have been used. Unfortunately, the fact is that if the disposal of the material depends on the user's desire, the patient will lack every possible protection. In other words, if the user wants to reuse the syringe, he or she will.

Non-reusable syringes of different types are known, such as those which withdraw the needle within the cavity of the barrel, in such a way that said needle obstructs the operative function of the syringe, as well as the fact that the needle becomes useless by itself. Likewise, there exists non-reusable syringes in which the piston, after the first suction and compression, meets a blocking mechanism which prevents a new withdrawal. The piston is rendered useless against the bottom of the barrel, without any possibility of motion. In spite of the operating advantages provided by these known syringes, practice has demonstrated that those syringes present various problems which go against their acceptance and practice.

One of these problems is the one arising from a major structural complexity as, even in the case of syringes which are functionally efficient, these demand a complex process of construction; which apart from limiting the massive production, considerably raise the costs of production; these facts, undoubtedly, are against the disposable condition of the product which requires, to such effect, a low cost of production.

Another problem to be considered, pertaining also to the final costs of the product, is the one that refers to the practibility of the manufacturing process. That, taking into account that there exist syringes structures that, although they have a device limiting the number of strokes, the effectiveness of which can be demonstrated in a prototype, the truth is that they greatly complicate the conventional productive processes and they oblige to create and develop new machinery and construction methodology, making substantial investments to such effect, everything with a considerable increase of the operative and productive costs and, besides, with an uncertain result.

SUMMARY OF THE INVENTION

The new syringe object of this invention, is a non-reusable type of syringe. The piston and its stem are separated by a mechanic fuse through an engaging and disengaging mechanism of the piston with respect to the stem. The engaging and disengaging mechanism is operated by the normal movement of the piston and the stem in its suctioning and ejection action, providing means of keeping the stem within the syringe barrel. Moreover, this mechanism limits the strokes and is composed of two pieces that, apart from being respectively attached to the piston and the stem, are linked between themselves by a guiding mechanism which is joined to the stem and a guided mechanisms which is joined to the piston. The guiding and guided mechanism form a passage which has a first retaining section and a second section for releasing the guided mechanism includes two bolts placed in an end or rear end of the piston, and mounted on a system of reversible support mechanisms.

This new way of establishing a circumstantial link between the piston and the plunger, is much simpler, easy to manufacture and it is safer than conventional syringes. The guided mechanism can be inserted into the guiding mechanism in accordance with the present invention, in such a way that it can be manually constructed by simple mechanical devices, in a quick way, with a high production and at a very low cost.

Likewise, and with an equivalent level of constructive simplicity, the present invention, anticipates the production of non-reusable syringes with the indicated characteristics, but with the capacity of being useful for more than a complete stroke (for example 2 or 3 strokes). This is necessary for the case when it is necessary to subsequently inject the same or different medicines, or mix them, and with respect to the patient, in subsequent suctions and ejections.

This is the case of medicines that include the syringe for its specific application; being prepared for the exact number of complete strokes that the mixture requires, after which the plunger will become separated from the piston. To such effect it shall include more than a guiding mechanism (one per stroke), combining their respective slides among themselves. Through these additional improvements, a non-reusable syringe has been achieved, without the voluntary intervention of the user, that allows the movement of the piston and the plunger without putting into motion the mechanism that produces the disposal of the syringe, presenting a proper handling of the syringe in the steps previous to the load of the liquid to be injected.

The operation of the releasing mechanism is produced when the liquid is loaded through the needle put in the syringe and when the liquid is ejected through the same for its application to the patient.

Therefore, the acceptance that the new improved syringe will have when put into practice is to be imagined, whatever the category and destine may be, as for its characteristics, the same is equally presented to be applied as a non-reusable syringe without any voluntary intervention of the user and of limited and predetermined strokes, for medical or surgical use, in human medicine and even veterinary medicine.

BRIEF DESCRIPTION OF THE DRAWINGS

The object of this invention is illustrated with many Figures in which it has been shown in one of its preferred ways of embodiments, in order to be clearer and better understood, everything shown is an illustrative example, not limitative.

FIG. 1 is a longitudinal sectional view of the barrel, showing the end of the plunger supplied by the guiding mechanisms, before being inserted through the bolts that are separated before being reversible according to the arrows, in case of inserting the piston and the end of the plunger through the rear opening of the barrel.

FIG. 2 is another longitudinal sectional view of the barrel, corresponding to the forward end which continues with the adapter for a attachment of the needle. In this Figure, one can see the piston with its guiding mechanisms already connected to the end of the plunger through the guided mechanism (bolt) that is closed according to the small arrows so that the sections end establishing a single guided bolt.

FIG. 3 is a longitudinal sectional view of the syringe constructions, and with the wings that close the opening of the rear end reversed, showing the guided position of the bolt within the clip, when the first suction stroke is produced.

FIG. 4 is a sectional view similar to FIG. 3, but showing the guided position of the bolt when the piston must move as the arrows indicate for the compression operation i.e., for injecting).

It is observed that, in these circumstances, the bolt gets derailed according to the small arrow, coming out from the guiding mechanism.

FIG. 5 is a sectional view similar to FIG. 3, but showing the position in which the bolt has been disengaged from the guiding mechanism and leaves the piston free from the plunger and incapable of reuse.

Figure 6:
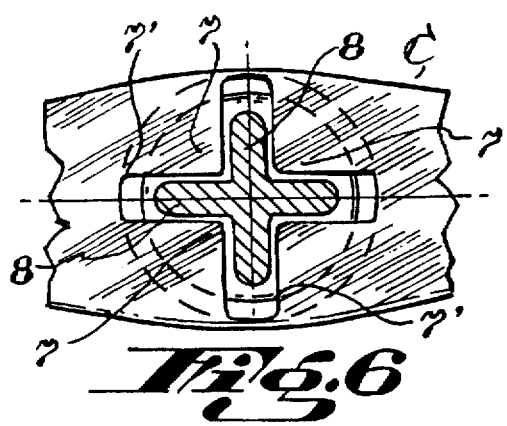

FIG. 6 is a sectional view of the plunger observed according to a plane indicated as VI—VI in FIG. 3, allowing to observe the traverse view of the plunger, which directs itself to a passage formed for such purpose in the rear end entrance corresponding to the cylinder.

Figure 7:
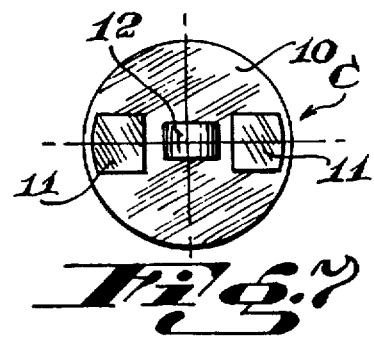

FIG. 7 is a view of the end of the plunger and its guiding mechanisms, observed according to what plane VII—VII in FIG. 5 indicates, showing how the guiding means is intercalated among the legs formed by stated end.

Figure 8:
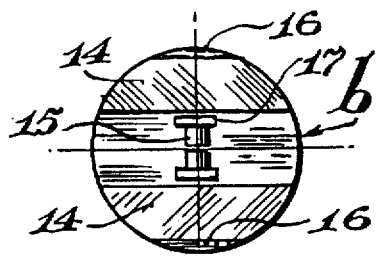

FIG. 8 is a view of the piston base according to the plane indicated as VIII—VIII in FIG. 5 provided at the same time by each projecting body that matching the arms forms a support of the parts which compose the bolt.

Figure 9:
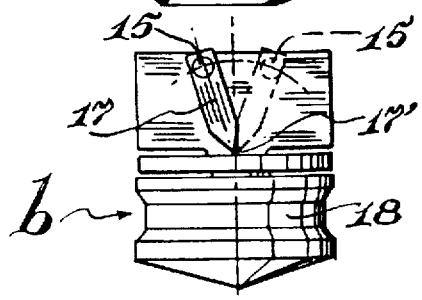

FIG. 9 is a view of the piston and its back zone, without one of the bodies which compose it to show the way in which the arms supporting the portions of the bolt are connected in an articular way with the base of the piston.

Figure 10:
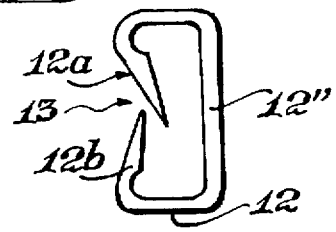

FIG. 10 is a side view of the guiding mechanism to observe its configuration in open "9" and disposition of the different parts which form it defining the different guide parts of the bolt, according to the position of the piston.

Figure 11:
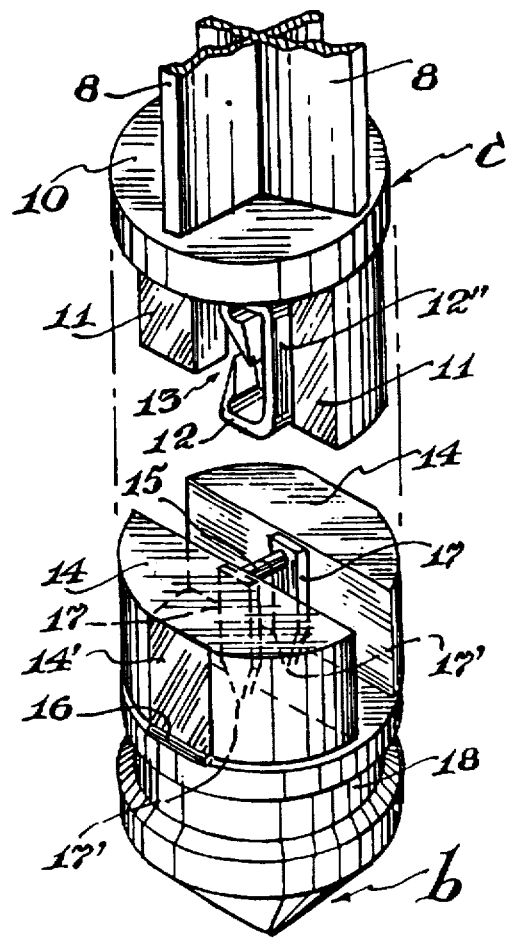

FIG. 11 is a detailed perspective view of the device of the present invention, which comprises the end of the plunger in which the guiding mechanism and the unlatching bolt which constitute the guided mechanism are mounted; and mounted in a support provided by the rear end of the base of the piston.

Figure 12:
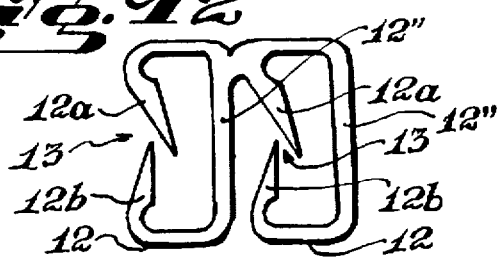

FIG. 12 illustrated in detail the guided mechanism in its embodiment for two strokes.

FIG. 13 shows a longitudinal sectional view of a syringe barrel and fragmentary sectional views of the piston which include the guiding and the guided mechanism of this invention.

FIG. 14 is a sectional view of the piston by line II—II of FIG. 13 and it shows the guiding mechanism and the guided mechanism separately.

FIG. 15 is a sectional view similar to FIG. 14, where the process of construction of the guiding mechanism with respect to the guided mechanism is shown.

FIG. 16 is a view in lateral elevation of the guiding mechanism in its position of assemblance with the guided mechanism.

FIG. 17 is a view similar to FIG. 16, where the portion of the guided and guiding mechanisms in the ejection movement is illustrated.

FIG. 18 is a view similar to FIG. 16, where the position of the guided and guiding mechanisms are illustrated, showing the projection of the guided mechanism in its retaining position in dotted lines and in half retaining position in a complete line.

FIG. 19 is a view similar to FIG. 16, where the position of the guided and guiding mechanisms are illustrated, showing the projection of the guided mechanism in a complete line in its releasing and disengaging position of both when the ejection stroke is produced.

FIG. 20 shows the disengaging position of the guiding and guided mechanisms and the retention effect of the plunger within the syringe barrel.

FIG. 21 shows a view in upper plane of the guided mechanisms.

FIG. 22 shows a view in lower plane of the guiding mechanisms.

FIG. 23 shows a lateral view in elevation and a fragmentary sectional view of the guiding mechanisms.

FIG. 24 is a perspective view of the guided and guiding mechanisms in their disengaging position.

OBJECTS OF THE INVENTION

IMPROVEMENTS IN HYPODERMIC NON-REUSABLE SYRINGES WITHOUT VOLUNTARY INTERVENTION OF THE USER AND WITH PREDETERMINED LIMITATION OF STROKES, of the type that comprises an elongated barrel (a) which, in one part is comprises rear end opening (7'), while in the opposite end it is closed with a bottom (2) provided with a perforation (2') extending through an external tubular adapter (3) in which a tubular needle 4 is engaged as a channeling mechanism of the liquid contained in the barrel (a). Barrel (a), gives a sliding direction to a piston (18) connected with a controlling stem (8). The opposite end of stem (8) projects through the rear end opening (7'). Piston (18) is connected to its stem (8) through an engaging and disengaging mechanism of the piston (18) with respect to the stem (8) that operates by the normal movement of the piston (18) and the stem (8) in its suction and ejection. A retention mechanism of the stem (8) is supplied within the barrel (a) of the syringe in an area which does not interfere with the normal operation of the piston and the stem.

Another additional object of this invention is an engaging and disengaging mechanism which comprises a guiding mechanism joint with the plunger and a guided mechanism joint to the piston. The guiding mechanism forms a passage which has a first retaining portion and a second releasing portion of the guided mechanism.

Another additional object of this invention is the fact that the guided mechanism is formed by a support placed in the passage of the guiding mechanism that is connected to the piston in a laterally displacing way with respect to the alternate movement of the piston.

Another additional object of the present invention is the fact that the support comprises two bolts, one disposed opposite the other, placed in the passage of the guiding mechanism. Each connected by its external end to each leg elastically articulated to the upper base of the piston.

Moreover, another additional object of the present invention is the fact that the piston is formed by a circular base which, in its surface opposite to the fixing of the legs, has a retaining mechanism of a cylindrical body constituting the piston itself which makes contact in an hermetically displacing way with the inner wall of the barrel.

Another additional object of the present invention is the improvements in hypodermic non-reusable syringes of the type that comprise an elongated barrel which, in one end is open while in the opposite end is closed with a bottom provided with a pipe through an external tubular adapter for the engagement of a needle. A piston is placed in a sliding way in the control barrel by a plunger. The opposite end of the plunger projects further than the opening end of the barrel. The piston is connected to the plunger through an engaging and disengaging mechanism of the piston with respect to the plunger by a retaining mechanism of the plunger within the syringe barrel in an area which does not interfere with the normal operation of the piston and the stem. The engaging and disengaging mechanism including a guiding mechanism joint to the stem and a guided mechanism joint to the piston the guiding mechanism has a passage which has a first retaining portion and a second releasing portion of the guided mechanism and the guide mechanism held by a projection placed in the passage of the guiding mechanism. In the passage, an elastic retaining mechanism of the projection are placed, which is capable of allowing the movement of the piston, in accordance with an established condition and the release of the projection in accordance with another established condition. A retaining mechanism is used for the displacement of the projection in the retaining and releasing portions of the passage of the guiding mechanism.

DETAILED DESCRIPTION OF THE PREFERRED EMBODIMENT

This invention relates to improvements in hypodermic non-reusable syringes without voluntary intervention of the user with predetermined limitation of strokes, as well as the quick construction method of the syringes.

The improvements have been practiced in a syringe comprising an elongated barrel (a) that, while in one end it has a rear end opening (7') in the opposite end it is closed with a bottom (2). Bottom 2 is provided with a prolonged perforation (2") through an external tubular adapter (3). Adapter (3) engages a needle (4) which constitutes a channeling mechanism or means of the liquid contained in the barrel (a).

Barrel (a) gives a sliding direction to a piston (18), which is connected to a controlling plunger (8). Plunger (8) has a body formed as radially expanded ribs that by its opposite end it is projected through the rear end opening (7') to finish in the final thrust end (9) of the plunger (8).

Furthermore, the piston (18) is connected to the plunger (8) through an engaging and disengaging mechanism and limiting of strokes which is comprised by two sets of pieces: the guiding means (c) and the guided mechanism or (b).

The guiding mechanism (c) is formed by the plunger (8), by the support base (10) which is placed in the inner end of said plunger (8) by the thrust legs (11) and by the guiding member (12). Guiding member (12) is joined to the central area of the support base (10). The trust legs (11) are placed on both sides of the guiding member (12) and in a coplanar position with the guiding member 12.

In a more detailed way the guiding member (12) is an elongated piece of adequate width which as a longitudinal portion (12"), approximately directed parallel to the geometrical longitudinal axis of the barrel (1). An upper elbow of member 12 is fixed to the lower surface of the support base (10) which finishes in a lateral portion (12a) directed against the support base (10) and slightly displaced towards the longitudinal portion (12"). A lower elbow of member 12 is disposed opposite to the upper elbow which finishes in a lower lateral portion (12b) opposite to the longitudinal portion (12"), and directed towards the support base (10), but which is externally overlapping the end of the lateral portion (12a) of the upper elbow. An empty space is disposed between both the lower elbow and the upper elbow. The thickness of upper (12a) and lower (12b) lateral portions is such that it allows an elastic displacement of their ends, so that then they can return to their initial position.

Upper portion (12a), the upper elbow and the longitudinal portion (12") form the retaining portion of the guided mechanism (b) and the lower portion (12b) with the end directed towards the inside of the upper section (12a) forms the releasing portion of the guided mechanism (b).

The mechanism is, in one exemplary embodiment, a bolt (15) divided in two complementary sections designed in projection from each support leg (17). Legs 17, on one hand, finish in ends (17') which articulate in the base (18') of the piston (18). In this way, the bolt (15) is placed in the central area of base (18") and within a deep neck formed by two bodies (14) of circular external outline and internally flat which are projected from the base (18'). Bodies (14) are joined by their circular outline by articulations (16) with the base (18") of the piston (18).

In different ways of embodiment, two or three guided mechanisms (12) combined among themselves can be placed, which define outlet (13) channels of the piston (15), corresponding to two or three complete strokes, respectively, as is shown in FIG. 12. On the other hand, in the other end of the syringe, the rear end opening (7'), constitute retaining tops of the piston (18) in the assembled syringe.

In a different embodiment, the wings (7) can be replaced by deformations of the lateral wall (1) of the barrel (a) towards the inside of the barrel (a).

OPERATION OF THE SET

The set operates in the following way:

The folding wings (7) of the rear end (7') opening of the barrel (a) are open, when the guided set (b) and the guiding set (c) are inserted into barrel (a) (see FIGS. 1 and 2). The bodies (14) of the piston (18), which are open, are dismantled by the walls (1) of the barrel (a) in such a way that, in turn, they dismantle the support legs (17) of the bolt (15). Consequently, the complementary portions of said bolt (15) approach closing within the guiding member (12) of the guiding set (c).

As the set within the barrel (a) continues to move downward, the two portions of the bolt (15) join and together with the union area covered by the guiding means (12) they are placed against the end of member (12) next to the support base (10). Once the piston (18) bumps into the bottom (2) of the barrel (a), the suction stroke begins, and the bolt (15), which is now placed in the member (12), moves against the end of member (12) distant from the supporting base (10).

Once the suction is over, the compression operation (to inject) begins with the plunger moves forward (i.e., downward as viewed int he drawing Figures). With this movement, the bold (15), which was placed against the end of the member (12) distant from the support base (10), moves along the longitudinal portion (12") until the height of the lateral portion (12a), where the proximity of the last one with the longitudinal portion (12"), diverts a portion of the bolt (15) which goes into an outlet channel (13) limited by both extreme teeth (12a) and (12b).

This construction determines that the movement of the bolt (15) shah lead it to the outlet of the guiding means (12) and, therefore, causes the disengagement between the plunger (8) and the piston (18).

ASSEMBLY METHOD

Regarding to the method, it consists in that the piston (18) of the guided set (b) goes into, the rear end opening (7') of one of the ends of the syringe barrel (a). After that, the guiding means (12) is placed by leaning it on the central area of the base (18') of the piston (18), in such a way that the bolt portions (15) projected from the support legs (17) face the slides formed by the longitudinal portion (12") and the teeth (12a) and (12b) of the guiding means (12).

Then, from the plunger (8), the piston is pushed (18) inserting it in the barrel (a) and forcing with the own lateral walls (1) of the barrel (a), the rebuttal of the bodies (14) and the support legs (17) which are open, until they close making the insertion of the portions of the bolt (15) within the slides formed by the guiding mechanisms (12).

Finally, the folding wings (7) limiting the rear end opening (7') of the barrel (a) in connection with the radial ribs of the plunger (8) are folded, which, in some ways of embodiment, can be made by means of a heating method that fixes the folded position of the folding wings (7).

A preferred way of embodiment of the improvements in hypodermic non-reusable syringes, without the voluntary intervention of the user, and without limitation of strokes except for the ones charging and discharging the liquid under pressure, is the one referred to hereafter with reference to FIGS. 13–24.:

The syringe to which the improvements have been applied comprises a conventional barrel (120), which in its end has an adapter (121) to engage the needle (not illustrated) in a free removable way, also conventional. In the opposite open end of the mentioned barrel (120), an also conventional flange (122) is placed, through where the stem (124) of the piston (123) moves. The piston is provided with a disk (125), the diameter of which is slightly smaller than the inner diameter of the barrel (120), and limits the plunger (124) stroke, when it pumps into at least two entrances (126) placed in the wall of the barrel (120) adjacent to the flange (122) of the open end of barrel (120).

The piston (123) is composed of a guiding set (149) and a guided set (150). The guiding set (149), as illustrated in FIG. 23, is composed of a disk (125) that, in its free surface (126), has a body (127) that projects radially. Body (127) extends from the outline of the disk (125) up to a little bit more than the central axis Of the barrel (120), and which ends in a projection (128) that is folded towards the disk (125), in a way that is parallel to the virtual axis of the barrel (120), while remaining at a prudential distance from the free surface (126) of the disk (125). The width of body (127) is substantially smaller than the radius of disk (125) and in its lateral walls (129), it is provided with each groove (130), which extends the inner wall (132), which presents an inclined plane ending in the projection (128).

From the free surface of the disk (125), a wing (133) projects, the width of the wing is the same as the one of the body (127), and it extends from the semicircumference opposite to the body (127), adjacently of the longitudinal axis of the barrel (120), under the projection (128) and facing the inner wall (132) of the body (127), leaving a free space (136) with the end of the projection (128).

The guided set (150) is composed of a conventional cylindric cap (137), which in its surface opposite to the adapter (121) has a disk (138) joint to the cap (137). The disk (138) in its free surface has two projecting bodies (139), the transverse sections of which are circular segments and they are stuck to the disk (138) by an extension (140) of the contiguous outline of the curved surface (141) of projecting bodies (139) is slightly bigger than the width of the body (127), and they are slightly higher than body (127).

On the diameter of the disk (138) perpendicular to the referred flat surfaces (142), two supports (143) are placed in a facing way, adjacent to the flat surfaces (142), which end in each cylindric projections (144), perpendicular to the supports (143) and in a same line facing each other, and leaving a free space between themselves. The joint of the supports (143) to the free surface of the disk (138) is such that is allows a radial movement of them in a way parallel to the flat surfaces (142).

It is important to notice that the diameter of the cylindric projections (144) is slightly bigger than the free spaces (134) and (136) of the guiding set (149), in such a way that the passage of the cylindric projections (144) through the free spaces (134) and (136), should be done pursuant to certain conditions of pressure in the guided mechanism (150) and in the guiding mechanism (149), respectively.

The assembly process of the syringe consists, firstly in engaging the guiding set (149) with the guided set (150), and then in the insertion of the piston (123) so formed, by pushing the plunger (124), up to the inside of the barrel (120). Once the disk (125) has been placed beyond the flange (122), the deformation of the wall of the barrel (120) is made, producing the entrances (148), which impede the removal of the piston (123) and the stem (124) from the inside of the barrel (120). The engagement of the guiding set (149) with the guided set (150) is performed in the way illustrated in FIG. 15, where the cylindric projections (144), fact the grooves (130) and they slide laterally along the same towards the inner wall (132) of the body (127) together with the other elements of the guided set (150), for elastically forcing the supports (143) in the last portion of the lateral walls (129) before reaching its assembly position, that is when the projections (144) are placed in the space limited by the free surface (126) of the disk (125), the inner wall (132) of the body (127) and the wing (133), as is illustrated in FIG. 16.

OPERATION

Once the syringe has been assembled as described above, the syringe operates as a conventional syringe. The piston (123) is able to move through its stem (124) within the barrel (120), with the sole limitation that the piston (123) is not able to go far from the entrances (148) adjacent to the flange (122). This is possible because within the movement of the piston (123) for the expulsion of the liquid contained in the barrel (120), the cylindrical projections (144) lean against the free surface (126) of the disk (125) and through the supports (143) projections (144) transmit the movement to the guided set (150), which is completed with the thrust of the body (127) and thrust projection (145) placed in the disk (125), against the free surface of the disk (138) between the projected bodies (139) the free surfaces of which lean against the empty surface (126) of the disk (125).

In the movement of the piston (123) for the suction of liquid, through the adapter (121), without the application of the syringe allows to maintain the guiding (149) set engaged with the guided (150) by virtue of the cylindrical projections (144) are retained between the end of the wing (132) and the inner wall (132) of the body (127, as the empty space (134) is smaller than the diameter of the cylindrical projections (144).

When the needle is applied to the adapter (121), the suction flow is obviously considerably reduced, therefore a depression is caused between the adapter (121) and the stopper (137) of the guided set (150). The depression displaces the piston (123) in the suction movement of the liquid. This depression as it has been caused, tends to retain the guided set (150) against the displacement of the guiding set (149) so, therefore, the cylindrical projections (144) are forced through the space (134), the end of the wing (135) becoming loose, leaving in this way the cylindrical projections placed against the projection (128) as is illustrated in FIG. 18. Once the syringe has been filled with the liquid to be injected and once the needle has been stuck onto the patient's body, the movement needed for the injection of the liquid existing between the stopper (137) of the guided set (150) and the adapter (121) is started, causing a pressure area, as pressure is exercised in the guiding set (149) through the piston (123) as the outlet of the liquid is limited by the reduction of flow which the use of the needle implies, plus the resistance to the inlet of liquid in the patient's body. The pressure area makes the cylindrical projections (144), that were placed in the inner cavity which forms the projection (128), displace up to the surface (135) of the wing (133) and that overcoming the elastic resistance of the projection (128) they pass through the free space (136) as illustrated in FIG. 19, producing a disengagement of the guiding set (149) with respect to the guided set (150) as illustrated in FIG. 20. The retention exercised by the entrances (148) obstructs the withdrawal of the plunger (124), so, in this way, the syringe may not be disassembled, becoming useless for being reused. It is important to notice that the disengagement of the guiding (149) and guided (1500 sets is produced without the voluntary intervention of the person applying the injection, as the disengagement is produced with the natural movements of suction and injection of the liquid in the syringe.

It is obvious that once this invention is taken into practice, modifications as regards certain construction and form details may be introduced, without this implying that the main principles clearly sustained in the following claims may be left aside.

I claim:

1. An autodiscardable hypodermic syringe with preset piston stroke limitation, comprising:

an elongated cylinder having an opened end and an opposite substantially closed end;

an external tubular mouthpiece having a conduit for the coupling of a needle to said substantially closed end;

a piston being slidably received in said cylinder;

a rod for sliding said piston being selectively connected to said piston, an end of said rod remote from said piston projecting beyond said open end of said cylinder, said piston being selectively connected to said rod through a coupling and uncoupling mechanism, said coupling and uncoupling mechanism comprises a narrow body that projects from the internal end of the rod and has a passage coincident with a central axis of said rod, said passage extends from side to side of said narrow body and defines a descending section, that in its middle part has a deviation disposed outward of the descending section and of said narrow body;

said piston being provided with a cavity for housing said narrow body and a hook in said passage being displacable from said descending section and through the deviation outward from the passage during the expulsion movement; and retention means for retaining said rod in said cylinder being provided within the cylinder of the syringe in an area that permits the normal operation of the piston and rod.

2. The autodiscardable hypodermic syringes with preset piston stroke limitation, according to claim 1, wherein said narrow body includes a portion that has a first horizontal section fixed to the internal end of said rod and continues with a first descending vertical section that has a free terminating end, said first horizontal section continues with a second descending vertical section that terminates in a second horizontal section that is parallel to said first horizontal section, said second horizontal section continues in a rising vertical section that terminates at approximately half of a length of said second descending vertical section and is disposed adjacent to the first descending section of the first horizontal section.

3. The autodiscardable hypodermic syringes with preset piston stroke limitation, according to claim 1, wherein said narrow body includes a base disk fixed to said internal end of said rod that has a descending projection that has two parallel faces that define, by an external side, an end wall next to an edge of said disk, and, by an internal side, an inclined surface from the surface of the disk, so that in a descending direction toward the central axis of the rod a rising projection is bent toward the disk, which is overlapping a fin that is originated in said disk oppositely to said inclined surface.

4. The autodiscardable hypodermic syringes with preset piston stroke limitation, according to claim 1, wherein said hook includes two faced spikes housed in said passage, each spike being resiliently articulated linked by a respective foot to a superior base of said piston.

5. The autodiscardable hypodermic syringes with preset piston stroke limitation, according to claim 4, wherein said piston is a circular disk that in its surface opposed to the linking of the foots has a retention means of a constitutive cylindrical body of the piston that contacts in an hermetically sliding way with an internal part of said cylinder.

6. The autodiscardable hypodermic syringes with limitation preset in piston stroke, according to claim 4, wherein the circular disk, between said foots and said internal wall of the cylinder, has a pair of bodies of circular external contour and a flat internal wall, said flat internal wall of each of said bodies being parallel with respect to each other, said bodies being articulated resiliently to the superior base of the circular disk of the piston.

7. The autodiscardable hypodermic syringes with preset piston stroke limitation, according to claim 4, wherein said fin that faces the inclined surfaces of the descending projection is resiliently movable to a passing of said spikes, a separation between the end of said fin and the inclined surface of the projection being slightly less than a diameter of said spikes.

8. The autodiscardable hypodermic syringes with preset piston stroke limitation, according to claim 2, wherein said rising vertical section and said first descending vertical section overlap each other at their respective ends.

9. The autodiscardable hypodermic syringes with preset piston stroke limitation, according to claim 8, a separation between both said rising vertical section and said first descending vertical section is slightly smaller than a diameter of said hook.

10. The autodiscardable hypodermic syringes with preset piston stroke limitation, according to claim 9, wherein said rising vertical section and said first descending vertical section are resiliently movable by a passing of said hook.

* * * * *